US012296116B2

United States Patent
Iverson et al.

(10) Patent No.: US 12,296,116 B2
(45) Date of Patent: May 13, 2025

(54) INTRODUCER HUB ASSEMBLY HAVING CROSS-SLIT SEAL

(71) Applicant: Pacesetter, Inc., Sylmar, CA (US)

(72) Inventors: Scott Iverson, Circle Pines, MN (US); Daniel Goodman, Minnetonka, MN (US); Daniel Coyle, St. Louis Park, MN (US); Scott Smith, Monticello, MN (US); Tracee Eidenschink, Wayzata, MN (US); Jennifer Heisel, Princeton, MN (US)

(73) Assignee: PACESETTER, INC., Sylmar, CA (US)

( * ) Notice: Subject to any disclaimer, the term of this patent is extended or adjusted under 35 U.S.C. 154(b) by 153 days.

(21) Appl. No.: 17/877,747

(22) Filed: Jul. 29, 2022

(65) Prior Publication Data

US 2022/0362517 A1    Nov. 17, 2022

Related U.S. Application Data

(63) Continuation of application No. 16/265,612, filed on Feb. 1, 2019, now Pat. No. 11,413,427.

(Continued)

(51) Int. Cl.
*A61M 25/00* (2006.01)
*A61M 39/06* (2006.01)
(Continued)

(52) U.S. Cl.
CPC ........ *A61M 25/0097* (2013.01); *A61M 39/06* (2013.01); *A61N 1/3756* (2013.01); *A61M 25/0662* (2013.01)

(58) Field of Classification Search
CPC .............. A61M 25/0097; A61M 39/06; A61M 25/0662; A61M 39/0606; A61M 2039/064; A61N 1/3756
See application file for complete search history.

(56) References Cited

U.S. PATENT DOCUMENTS

| 4,512,766 A | * | 4/1985 | Vailancourt | A61M 39/14 604/167.03 |
| 4,610,665 A | * | 9/1986 | Matsumoto | A61M 39/0606 604/167.04 |

(Continued)

FOREIGN PATENT DOCUMENTS

| EP | 1629787 B1 | 3/2010 |
| JP | 2002505920 A | 2/2002 |

(Continued)

*Primary Examiner* — Richard G Louis
(74) *Attorney, Agent, or Firm* — WOMBLE BOND DICKINSON (US) LLP

(57) ABSTRACT

An introducer hub assembly, such as an introducer hub assembly of a leadless cardiac pacemaker, including a hemostatic seal having a cross-slit configuration, is described. The hemostatic seal can be retained between a hub cap and an introducer hub. The hemostatic seal includes a first section having first slits intersecting along a longitudinal axis of the introducer hub, and a second section having second slits intersecting along the longitudinal axis. The first slits are angularly offset relative to the second slits to reduce a likelihood that fluid will leak directly through the seal. Other embodiments are also described and claimed.

17 Claims, 13 Drawing Sheets

Related U.S. Application Data

(60) Provisional application No. 62/628,154, filed on Feb. 8, 2018.

(51) Int. Cl.
*A61N 1/375* (2006.01)
*A61M 25/06* (2006.01)

(56) References Cited

U.S. PATENT DOCUMENTS

| | | | |
|---|---|---|---|
| 4,917,668 A * | 4/1990 | Haindl | F16L 37/38 |
| | | | 604/167.03 |
| 4,946,133 A | 8/1990 | Johnson et al. | |
| 5,112,308 A | 5/1992 | Olsen et al. | |
| 5,167,637 A | 12/1992 | Okada et al. | |
| 5,176,652 A | 1/1993 | Littrell | |
| 5,195,980 A | 3/1993 | Catlin | |
| 6,024,729 A | 2/2000 | Dehdashtian et al. | |
| 6,551,283 B1 * | 4/2003 | Guo | A61M 39/06 |
| | | | 251/149.1 |
| 6,632,200 B2 | 10/2003 | Guo et al. | |
| 6,712,789 B1 | 3/2004 | Lange et al. | |
| 7,850,653 B2 | 12/2010 | Hammond | |
| 7,985,232 B2 | 7/2011 | Potter et al. | |
| 8,105,287 B2 | 1/2012 | Fisher et al. | |
| 8,137,321 B2 | 3/2012 | Argentine | |
| 8,308,692 B2 | 11/2012 | McQueen et al. | |
| 8,430,811 B2 | 4/2013 | Hess et al. | |
| 8,430,812 B2 | 4/2013 | Barnes | |
| 8,690,831 B2 | 4/2014 | Duke | |
| 8,727,974 B2 | 5/2014 | Kasvikis | |
| 8,905,973 B2 | 12/2014 | Tegg et al. | |
| 9,055,933 B2 | 6/2015 | Escobar et al. | |
| 9,419,372 B2 | 8/2016 | Swanson et al. | |
| 9,554,825 B2 | 1/2017 | Fischvogt et al. | |
| 9,820,733 B2 | 11/2017 | Nolan et al. | |
| 2003/0050604 A1 * | 3/2003 | Lui | A61M 39/0606 |
| | | | 604/164.05 |
| 2006/0013596 A1 | 6/2006 | Kick et al. | |
| 2007/0085232 A1 | 4/2007 | Brustad et al. | |
| 2007/0276342 A1 * | 11/2007 | Lin | A61F 2/0027 |
| | | | 604/264 |
| 2008/0021532 A1 | 1/2008 | Kveen et al. | |
| 2010/0234688 A1 | 9/2010 | Carter | |
| 2010/0280456 A1 | 11/2010 | Nijland et al. | |
| 2011/0082344 A1 | 4/2011 | Barnes | |
| 2011/0166527 A1 * | 7/2011 | Wells | A61M 39/0613 |
| | | | 604/248 |
| 2013/0158348 A1 | 6/2013 | Nobis et al. | |
| 2016/0331935 A1 | 11/2016 | Saatchi et al. | |
| 2018/0142787 A1 | 5/2018 | Herzog et al. | |

FOREIGN PATENT DOCUMENTS

| | | |
|---|---|---|
| JP | 04885220 B2 | 2/2012 |
| JP | 05468342 B2 | 4/2014 |
| JP | 05492680 B2 | 5/2014 |
| JP | 05817066 B2 | 11/2015 |
| JP | 05898469 B2 | 4/2016 |
| JP | 06280041 B2 | 2/2018 |

* cited by examiner

INTRODUCER HUB ASSEMBLY HAVING CROSS-SLIT SEAL

This application is a continuation of U.S. patent application Ser. No. 16/265,612 filed on Feb. 1, 2019, which claims the benefit of priority of U.S. Provisional Patent Application No. 62/628,154, filed on Feb. 8, 2018, and these applications are incorporated herein by reference in their entirety to provide continuity of disclosure.

BACKGROUND

Field

The present disclosure relates to vascular access devices. More specifically, the present disclosure relates to an introducer hub assembly including a hemostatic seal.

Background Information

Some minimally invasive surgeries of the heart and blood vessels are accomplished using catheters with specialized functions. Catheters can enter the body from a site such as the femoral or jugular vein and travel to the inside of the heart or coronary arteries to fulfill their particular purpose. Many of these catheters, due to their unique geometries, require the use of a vascular access device, such as an introducer, that provides an entryway into the cardiovascular system (or other interior cavity of the body). The introducer can include a seal to prevent blood from escaping from the body while providing the entryway.

There are a variety of existing seal types that can be incorporated into an introducer to hold blood in the body while allowing a catheter to pass through the seal into the body from an external environment. For example, some hemostasis valves can include seals that are opened by an actuation force, such as an external compressive force, to force open the seal. Larger devices can be inserted through the open seal, and then the actuation force can be removed or reversed to close the seal.

SUMMARY

Difficulty arises when medical devices of several different sizes must pass through existing introducer seals at different times. For example, an introducer may first need to seal around a guidewire, followed by a much larger secondary cardiovascular device. Existing hemostasis valves can require the operator to squeeze or otherwise force the seal open, in order to make room for larger devices to be inserted, and then stop squeezing to restore the seal to a closed state. To operate the seal in this manner, the operator is generally precluded from using their hand to perform other tasks.

In an embodiment, an introducer hub assembly includes a hemostatic seal that allows the passage of progressively larger medical devices, e.g., cardiovascular devices, without the need for an operator to actuate the seal with an external force, such as a squeeze. The seal can be retained between an introducer hub and a hub cap of the introducer hub assembly. Accordingly, the seal provides a passage from an external environment, e.g., a catheterization lab, into an internal environment, e.g., a vasculature of a patient.

In an embodiment, the seal includes a cross-slit configuration. For example, the seal can include a first section having first slits that intersect along a longitudinal axis of the introducer hub, and a second section having second slits that intersect along the longitudinal axis. The second slits can be offset relative to the first slits. For example, the slit pairs, which may each be pairs of perpendicularly arranged cross slits, can be angularly offset such that the slits of one pair do not intersect or axially align with the slits of the other pair. In an embodiment, the angular offset of the first slits from the second slits is in a range of 40 to 50 degrees, e.g., 45 degrees. The offset cross slits can reduce a likelihood of leakage of a fluid from the internal environment by avoiding a direct pathway through the seal.

In an embodiment, the seal includes a tapered inner surface extending distally from a proximal opening at a proximal face of the seal toward a distal face of the seal. The tapered inner surface can taper toward the longitudinal axis, e.g., at an angle of 30 degrees from the longitudinal axis. The tapered inner surface can generally distribute force incurred by advancing larger objects through the seal, and direct such force in a radial direction.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The novel features of the disclosure are set forth with particularity in the claims that follow. A better understanding of the features and advantages of the present disclosure will be obtained by reference to the following detailed description that sets forth illustrative implementations in which the principles of the present disclosure are utilized, and the accompanying drawings of which:

DETAILED DESCRIPTION

Figure 1:
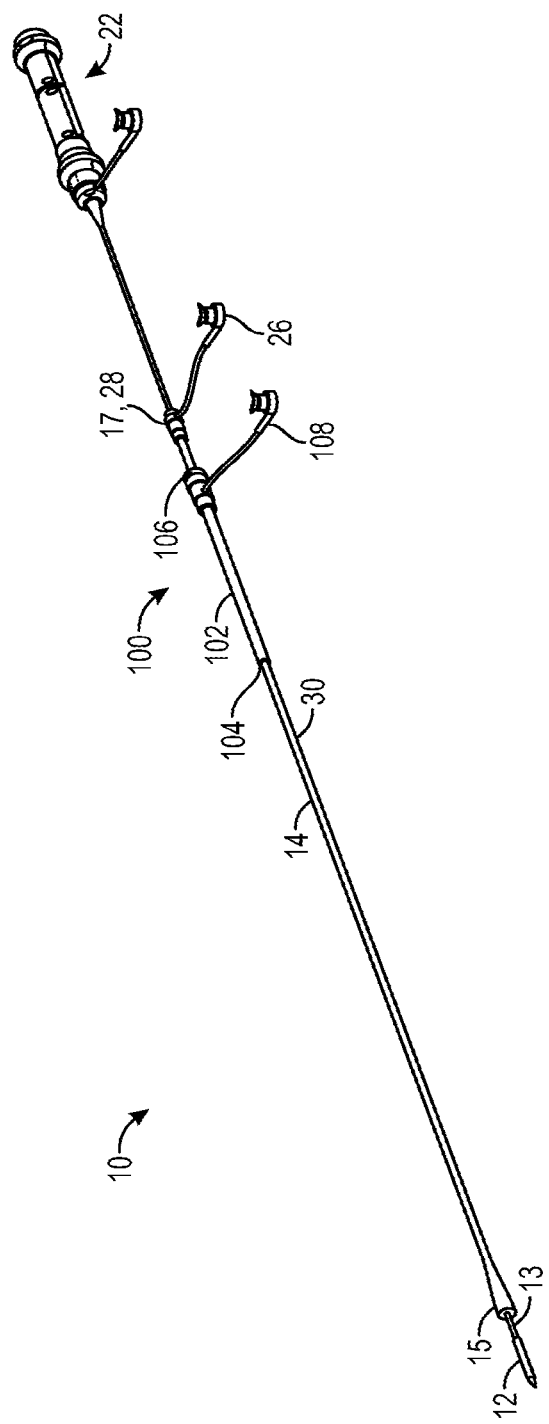
FIG. 1 is an isometric view of a leadless pacemaker system including an introducer hub assembly in accordance with the present disclosure.

Embodiments describe a seal having several sections, each section including slits that extend through the respective section and intersect along a longitudinal axis. The slits of each section can be cross slits offset relative to one another. The seal can be retained between an introducer hub and a hub cap of an introducer hub assembly. The seal, however, may be used in other applications, such as in a hemostatic valve assembly, an injection port, etc. Thus, reference to the seal as being used in an introducer hub assembly is not limiting.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction along a longitudinal axis of an introducer hub assembly. Similarly, "proximal" may indicate a second direction opposite to the first direction. Such terms are provided to establish relative frames of reference, however, and are not intended to limit the use or orientation of a seal or an introducer hub assembly to a specific configuration described in the various embodiments below.

In an aspect, an introducer hub assembly is provided. The introducer hub assembly includes a passive seal. The passive seal seals and provides hemostasis without a separate sealing device and accommodates a wide range of devices that may be introduced through the introducer assembly. The seal is generally made of a compliant material, such as silicone rubber, and has the ability to expand around objects that are advanced and retracted through the seal. The compliant material further allows the seal to recover to its original state when objects are removed from the seal. In certain implementations the seal has a proximal taper and slits to aid in centering and introducing objects through the seal while providing a hemostatic seal about the object. In addition, in certain implementations, the seal material may include various additives to further aid in the recovery of the seal to its original state following removal of objects therefrom. Such additives may also promote self-healing of the seal to improve the life of the seal and/or provide lubrication of the seal to reduce the forces necessary to introduce objects through the seal. In certain implementations, the introducer hub assembly may be constructed of an over-molded hub and hub cap made of an injection-moldable plastic material with the seal constrained and providing a hermetic closure between the hub and the hub cap. Accordingly, the introducer hub assembly does not require human intervention in order to seal around a wide range of different-sized devices.

Referring to FIG. 1, an isometric view of a leadless pacemaker system including an introducer hub assembly is shown in accordance with the present disclosure. A leadless pacemaker system 10 may be used for delivery and/or retrieval of a leadless pacemaker 12 into or from a patient, and can include an introducer hub assembly 100 in accordance with the present disclosure. The use of a system 10 for delivery and/or retrieval of a leadless pacemaker is merely intended as an example application of introducer hub assemblies in accordance with the present disclosure and primarily to provide context. It should be appreciated that introducer hub assemblies in accordance with this disclosure may be used to introduce or remove any suitable tools, medical devices, and the like into a patient and are not limited to leadless pacemaker applications.

The introducer hub assembly 100 may include an introducer sheath 102 and the system 10 may further include various catheters, such as, but not limited to, a deflectable catheter 13 and a guide catheter 14 adapted to be inserted through the introducer hub assembly 100 and, in particular, an introducer sheath 102 of the introducer hub assembly 100. As can be understood from FIG. 1, the guide catheter 14 may be slidably mounted on the deflectable catheter 13. For example, the deflectable catheter 13 may extend through the guide catheter 14. Similarly, the introducer hub assembly 100 may be slidably mounted on the guide catheter 14. For example, the guide catheter 14 may extend through the introducer sheath 102. A distal end of the deflectable catheter 12 may be selectively connectable to the leadless pacemaker 12 or other device, and a proximal end of the deflectable catheter 13 may include a handle 22 or similar tool by which a user may manipulate the deflectable catheter 13 or other elements of the system 10.

The guide catheter 14, which can extend through the introducer sheath 102 of the introducer hub assembly 100, includes each of a distal end 15 and a proximal end 17. The distal end 15 of the guide catheter 14 may include a protective pacemaker sheath. The proximal end 17 of the guide catheter may include a flush port 26 extending from a proximal hub 28. The guide catheter 14 extends from both the distal and proximal ends of the introducer sheath 102. A shaft 30 of the guide catheter 14 may also include one or more sections (not shown) having different durometers such that the reinforcement and corresponding bending resistance of the sections may be modified according to the specific application for which the system 10 is being implemented. The introducer hub assembly 100 further includes a distal end 104 and a proximal end 106. As illustrated, the proximal end 106 of the introducer hub assembly 100 may include a flush port 108. More particularly, a side port can extend from an exterior of an introducer hub to an interior cavity of the introducer hub, and the flush port 108 can connect to the side port to inject fluid into the interior cavity.

Figure 2:
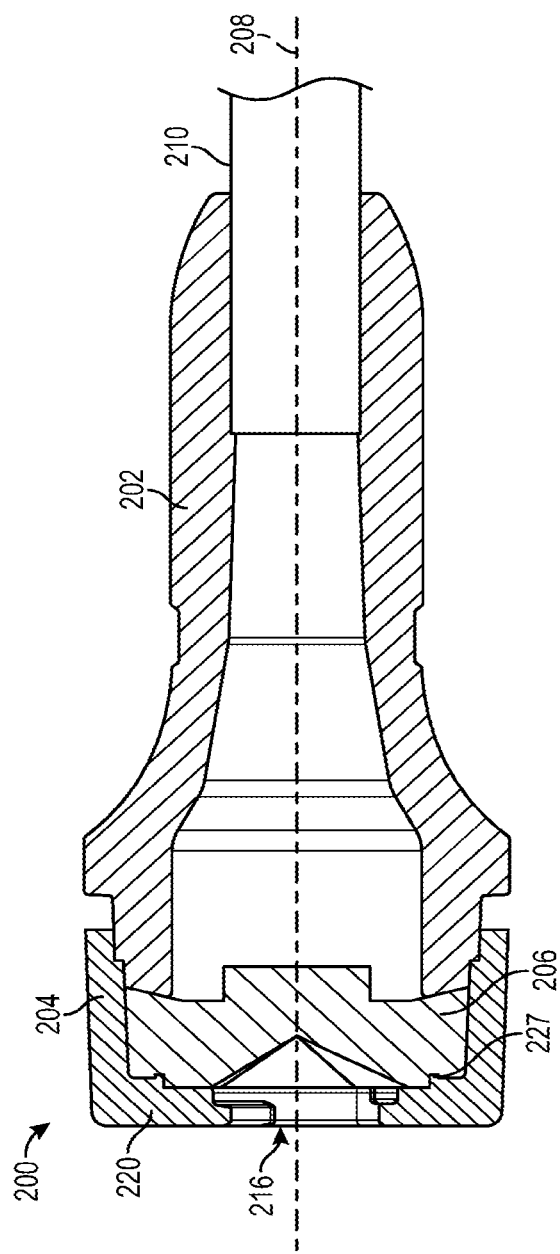
FIG. 2 is a longitudinal cross-sectional view of an introducer hub assembly including a seal in accordance with the present disclosure.
Figure 3:
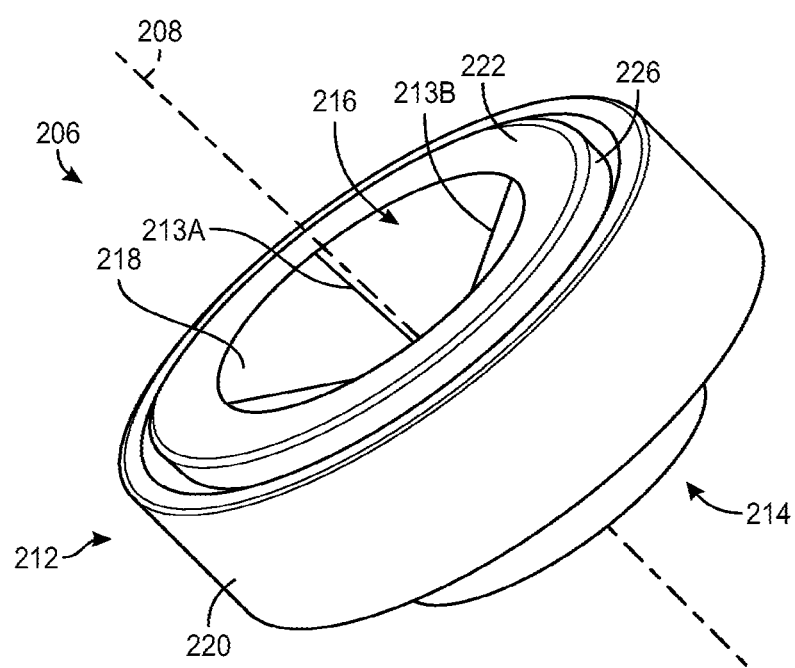
FIG. 3 is an isometric view of a seal in accordance with the present disclosure.

Referring to FIG. 2, a longitudinal cross-sectional view of an introducer hub assembly including a seal is shown in accordance with the present disclosure. The introducer hub assembly 200 includes an introducer hub 202, a hub cap 204 coupled to a proximal end of the introducer hub 202, and a seal 206 retained between the hub cap 204 and the introducer hub 202. The hub cap 204 can be coupled to the introducer hub 202 in numerous manners. For example, the hub cap 204 can be welded onto introducer hub 202, using a thermal, adhesive, or ultrasonic weld. Similarly, the hub cap 204 can be press fit onto introducer hub 202, or coupled to the introducer hub 202 by a snap fit feature or an external retaining ring, to name only a few possibilities.

For reference, the introducer hub 202 further defines a longitudinal axis 208. The introducer hub assembly 200 may further include an introducer sheath 210 extending from a distal end of the introducer hub 202. In certain implementations, one or both of the hub introducer hub 202 and the hub cap 204 are formed from a moldable plastic and are overmolded onto the seal 206 and/or the introducer sheath 210.

In certain implementations, the seal 206 is a hemostatic seal to prevent blood from passing through the seal when the introducer sheath 210 is inserted into a vasculature. The seal 206 can be formed from silicone rubber and generally allows for objects to be inserted through the seal 206 while maintaining a hemostatic seal. The seal 206 may have a specialized geometry that allows it to seal around objects of various dimensions. For example, in certain implementations, the seal 206 may be adapted to seal around cylindrical objects having a diameter from and including 0.035 inches to and including 0.3 inches. Notably, the seal 206 seals against such objects without requiring excessive force to advance such objects through the seal or requiring an operator to "open" the seal to make room for larger objects.

The seal 206 may include a proximal flange shaped to be received between the introducer hub 202 and the hub cap 204 when the introducer hub assembly 200 is assembled. As described below, a proximal face and/or a distal face of the seal flange 220 can be adapted to engage with, seal against, or otherwise interact with corresponding mating features of the introducer hub 202 and the hub cap 204, respectively. For example, the seal flange 220 can press against a protrusion 227 of the hub cap 204 to form a seal along the proximal face.

The seal may include a proximal opening 216. The proximal opening 216 may be disposed along the longitudinal axis 208, and can align with a corresponding opening in the hub cap 204. For example, the hub cap 204 opening can be coaxial with the opening 216 to allow a guidewire, catheter, or another device component to be inserted through the hub cap 204 and the seal 206 into an inner lumen of the introducer hub 202 and/or introducer sheath 210.

FIGS. 3-6 are various views of a seal shown in accordance with the present disclosure. The figures illustrate like features of the seal, and thus, are described together below. In certain implementations, the seal 206 is made of one or more compliant materials, e.g., a compliant silicone material. Such material(s) may have a durometer from and including 20 Shore A to and including 40 Shore A, thereby allowing the seal 206 to stretch and seal around objects of various sizes while providing sufficient durability to withstand multiple insertions/removals and manipulation of such objects, and to enable the seal 206 to return to its original shape and state when objects are removed from the seal 206. In certain implementations, the material of the seal 206 may also be selected to be at least one of self-healing and self-lubricating. The self-healing and self-lubricating properties of seal 206 can derive from the inclusion of various additives in the seal material to further aid in the recovery of the seal to its original state following removal of objects therefrom. Such additives may also promote self-healing of the seal to improve the life of the seal and/or provide lubrication of the seal to reduce the forces necessary to introduce objects through the seal.

The seal 206 generally includes a first, proximal section 212 and a second, distal section 214 adjacent to the proximal section 212. The distal section 214 can extend from a distal face of the proximal section 212. In certain implementations, one or more of the sections is substantially cylindrical. For example, the distal section 214 may be a substantially cylindrical section extending from a substantially cylindrical proximal section 212.

Figure 4:
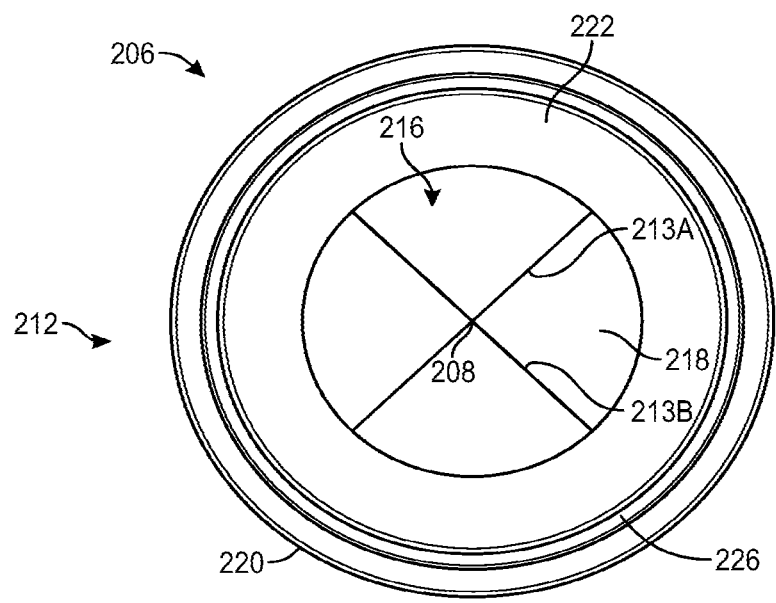
FIG. 4 is a proximal plan view of a seal in accordance with the present disclosure.

The seal can include slits extending through at least one of the sections. For example, the proximal section 212 can include a set of first slits, e.g., a pair of first slits 213A, 213B. The slits can extend through the proximal section and intersect along the longitudinal axis 208. Referring to FIG. 4, slit 213A and slit 213B can be straight lines when viewed in an end view, and the straight lines can cross at longitudinal axis 208. Accordingly, slits 213A, 213B can be cross slits. Similarly, the distal section 214 can include a second set of slits, e.g., a pair of second slits 215A, 215B, extending through the distal section 214 and intersecting along the longitudinal axis 208. For example, referring to FIG. 5, slit 215A and slit 215B can be straight lines when viewed in an end view, and the straight lines can cross at longitudinal axis 208. Thus, slits 215A, 215B are cross slits.

Figure 5:
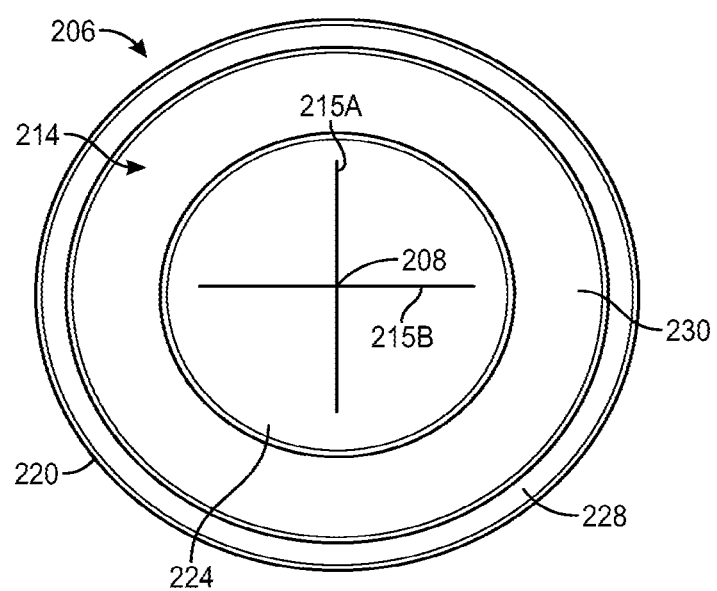
FIG. 5 is a distal plan view of a seal in accordance with the present disclosure.

The second slits 215A, 215B can be in an angularly offset orientation relative to the first slits 213A, 213B. This is evident from the "×" orientation of the slits 213A, 213B in FIG. 4 relative to the "+" orientation of the slits 215A, 215B in FIG. 5. More particularly, the "×" and the "+" are angularly offset because a clocking of the symbols differs with respect to a vertical line passing through the intersection point at the middle of the symbols. In certain implementations, such angular offset may be in a range of 40 to 50 degrees. For example, as shown in FIGS. 4-5, the first slits can be offset from the second slits by an angle of 45 degrees. In other words, the cross slits can be angularly offset with respect to each other.

Also shown in FIGS. 4-5, in certain implementations, each of the first slits 213A, 213B may extend perpendicular with respect to each other and each of the second slits 215A, 215B may similarly extend perpendicular with respect to each other. Perpendicularity refers to, for example, the angle between slit 213A and slit 213B, which is 90 degrees in FIG. 4. The angle between slits may vary, however. For example, the individual slits of one or more of the slit pairs may be separated by an acute and/or obtuse angle. Nonetheless, in certain implementations, no slit of the first slit pair is coplanar with a slit of the second slit pair within a plane defined by the slit of the first slit pair and the longitudinal axis 208.

Figure 6:
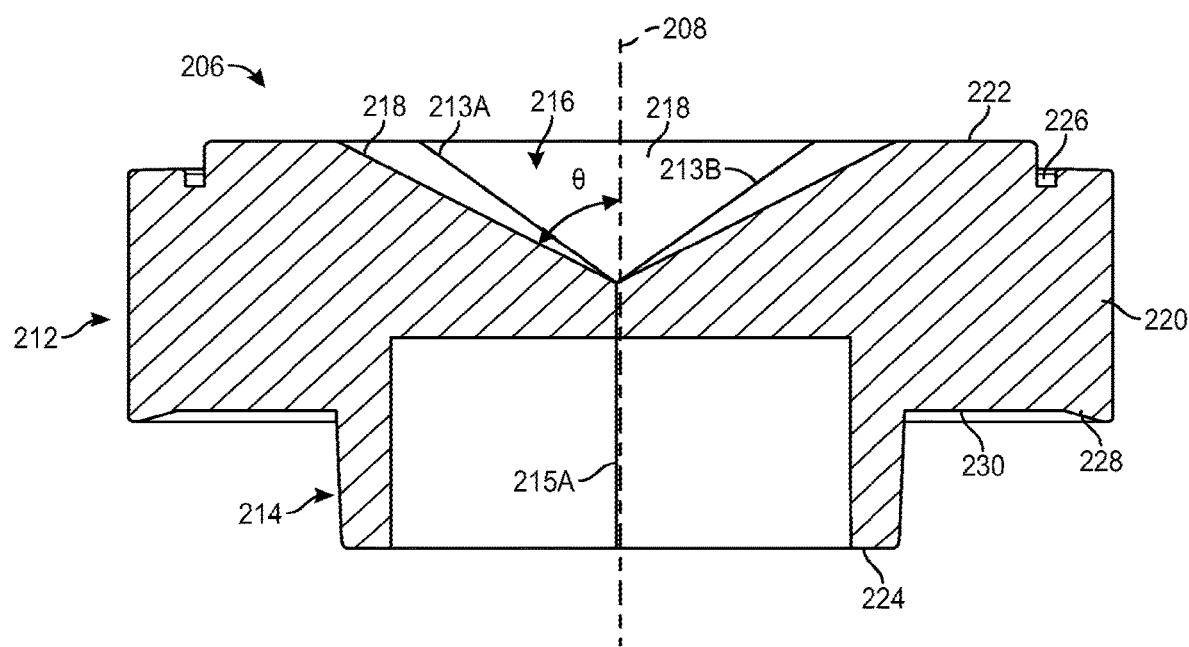
FIG. 6 is a cross-sectional side view of a seal in accordance with the present disclosure.

Referring to FIG. 6, in certain implementations, the slits 213A, 213B and 215A, 215B are not cut completely through the seal 206 and prevent a direct pathway for blood flow through the seal 206 when the seal 206 is each of a closed state (unused) as well as an open state (in which an object is inserted through the seal 206). Slits 213A, 213B may extend from proximal face 222 to an intersection point at longitudinal axis 208 that is proximal to distal face 224 of seal 206. Similarly, slits 215A, 215B may extend from distal face 224 to an intersection point at longitudinal axis that is distal to proximal face 222. Accordingly, in an embodiment, neither slit pair extends entirely through a thickness of seal 206. The slit pairs may overlap, however. For example, a depth of the first slit pair 213A, 213B may be greater than half of the seal thickness and a depth of the second slit pair 215A, 215B may be greater than half of the seal thickness. The first slit pair therefore overlaps a depth of the second slit pair. Although overlapping in the axial direction, the slits may not be axially aligned with each other (they may be angularly offset), and thus, the cross slit pairs may be oriented to limit the pathways along which fluids can propagate through the seal thickness.

During operation, the slits 213A, 213B and 215A, 215B in combination with the structure of the proximal and distal sections 212, 214 make use of the elastic force provided by the material of the seal 206 and the hydrostatic pressure within the introducer hub 202 to recover the seal 206 after objects are retracted and removed from within the seal 206. More particularly, a substantially cylindrical section of the seal 206 can use hydrostatic pressure and the elastic force provided by the material itself to recover the seal after objects are retracted and removed from the seal.

The seal 206 may include a tapered inner surface 218 extending distally from the proximal opening 216 at the proximal face 222. The tapered inner surface 218 can taper from the proximal opening 216 toward the longitudinal axis 208. In certain implementations, a portion of the tapered inner surface 218 may extend through at least a portion of the proximal section 212. The first slits 213A, 213B can extend through at least a portion of the tapered inner surface 218. Referring to FIG. 6, the inner surface 218 may be tapered relative to the longitudinal axis 208. An angle θ between the inner surface 218 and the longitudinal axis 208 can define the taper of the inner surface 218. In certain implementations, the angle θ may be in a range of 25 to 35 degrees, e.g., 30 degrees. The tapered inner surface 218 provides a recess, indentation, or lead-in in the seal flange 220. In general, the tapered inner surface 218 helps to center objects during insertion through the seal 206, thereby reducing a likelihood of premature damage to the seal 206, while also reducing a likelihood of fluid leakage from the seal 206 during insertion and removal of objects through the seal 206.

The proximal seal flange 220 can include a proximal face 222 and a distal face 230. The proximal face 222 and the distal face 230 may include respective mating features adapted to engage with, seal against, or otherwise interact with corresponding mating features of the introducer hub 202 and the hub cap 204, respectively. For example, in one implementation, the proximal face 222 may include a channel or a groove 226 shaped to receive a corresponding protrusion 227 (FIG. 2) of the hub cap 204. For example, the protrusion 227 can be an annular protrusion extending distally from an inner face of hub cap 204, and the annular protrusion may engage a corresponding annular groove 226. Alternatively, the protrusion 227 may press against a flat face of the seal flange 220 to form a seal between the hub cap 204 and the hemostatic seal 206. The distal face 230 may include a tapered flange 228 shaped to align the seal 206 along the longitudinal axis and to seal against the introducer hub 202. For example, the tapered flange 228 can be an annular protrusion that extends from the distal face 230 and tapers distally. A distal edge of the tapered flange 228 at an outer diameter of seal flange 220 is distal to a proximal edge of the tapered flange 228 at a location nearer to the distal section 214. When the introducer hub assembly 200 is assembled, the distal face 230 may, in certain implementations, be substantially in contact with an inner surface of the introducer hub 202, and the tapered flange 228 can press against the introducer hub 202, such that sealing between the seal 206 and the introducer hub 202 is further improved.

Figure 7A:
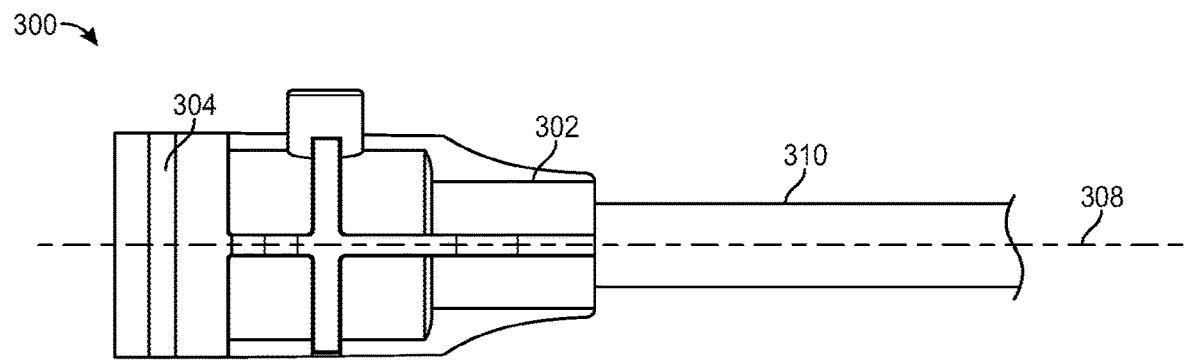
FIG. 7A is a longitudinal side elevation view of an introducer hub assembly in accordance with the present disclosure.

Referring to FIG. 7A, a longitudinal side elevation view of an introducer hub assembly is shown in accordance with the present disclosure. The introducer hub assembly 300 includes an introducer hub 302, a hub cap 304 coupled to a proximal end of the introducer hub 302, and a seal retained between the hub cap 304 and the introducer hub 302. For example, the seal may include a proximal flange that is retained between the introducer hub 302 and the hub cap 304. For reference, the introducer hub 302 further defines a longitudinal axis 308. The introducer hub assembly 300 may further include an introducer sheath 310 extending from a distal end of the introducer hub 302.

Figure 7B:
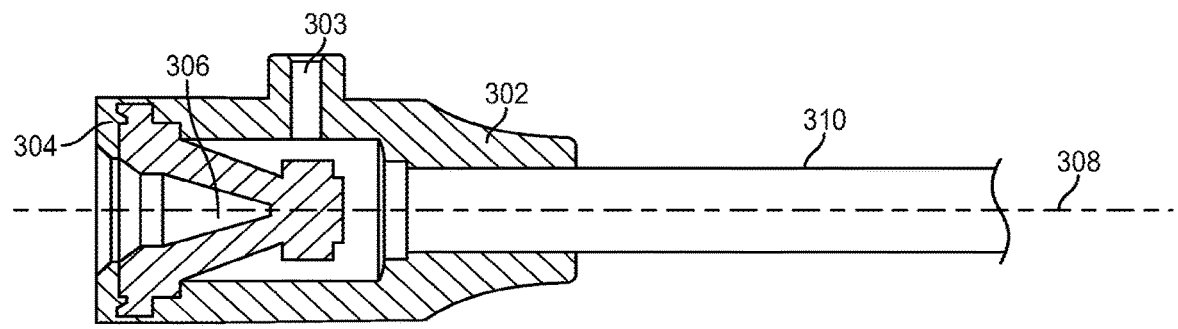
FIG. 7B is a longitudinal cross-sectional side view of the introducer hub assembly of FIG. 7A having a seal in accordance with the present disclosure.

Referring to FIG. 7B, a longitudinal cross-sectional side view of the introducer hub assembly of FIG. 7A having a seal is shown in accordance with the present disclosure. In certain implementations, one or both of the hub introducer hub 302 and the hub cap 304 are formed from a moldable plastic and are overmolded onto the seal 306 and/or the introducer sheath 310. The introducer hub 302 may include a port 303 or similar opening for providing and/or extracting fluids from an interior cavity of the introducer hub 302. For example, the port 303 can be a side port that extends from an exterior of the introducer hub 302 to the interior cavity of the introducer hub 302, which contains at least a portion of the seal 306. The port 303 can be in fluid communication with flush port 108 via a connecting tube.

In certain implementations, the seal 306 is formed from silicone rubber and generally allows for objects to be inserted through the seal 306 while maintaining a hemostatic seal. The seal 306 may have a specialized geometry that allows it to seal around objects of various dimensions. For example, in certain implementations, the seal 306 may be adapted to seal around cylindrical objects having a diameter from and including 0.035 inches to and including 0.3 inches. Notably, the seal 306 seals against such objects without requiring excessive force to advance such objects through the seal or requiring an operator to "open" the seal to make room for larger objects.

In certain implementations, the seal 306 is made of a compliant silicone material. Such a material may have a durometer from and including 20 Shore A to and including 40 Shore A, thereby allowing the seal 306 to stretch and seal around objects of various sizes while providing sufficient durability to withstand multiple insertions/removals and manipulation of such objects, and to enable the seal 306 to return to its original shape and state when objects are removed from the seal 306. In certain implementations, the material of the seal 306 may also be selected to be at least one of self-healing and self-lubricating.

FIGS. 8A-9B are various views of a seal shown in accordance with the present disclosure. The figures illustrate like features of the seal, and thus, are described together below.

Figure 8A:
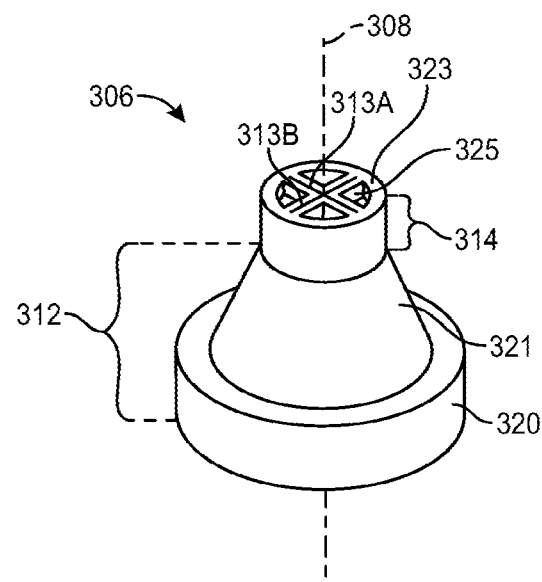
FIGS. 8A and 8B are distal and proximal perspective views, respectively, of a seal in accordance with the present disclosure.

Referring to FIG. 8A, the seal 306 generally includes a first, proximal section 312 and a second, distal section 314 adjacent to the proximal section 312. In certain implementations, the proximal section 312 includes a proximal flange 320 and a tapered body 321. The tapered body 321 can be adjacent to, and extend distally from, the proximal flange 320. The proximal flange can be retained between the hub cap and the introducer hub of an introducer hub assembly, as described above. The tapered body can be substantially conical. In an embodiment, the distal section 314 is a substantially cylindrical body adjacent to the tapered body 321. The distal section 314 can extend distally from the tapered body 321. A set of slits 313A, 313B can extend through at least the distal section 314. In an embodiment, the slits extend into the tapered body 321, and thus, extend through at least a portion of the proximal section 312. The slits of seal 306 can be similar to the slits of seal 206. In certain implementations, the slits 313A, 313B are cross slits oriented such that they are arranged substantially perpendicular with respect to each other. The slits 313A, 313B may not be cut completely through the seal 306 and may prevent a direct pathway for blood flow through the seal 306 when the seal 306 is each of a closed/open state. In certain implementations, the slits 313A, 313B are formed using a razor or similar blade.

In an embodiment, the seal 306 can include one or more pockets 325 in the distal face 323 of the seal 306. The distal face 323 can define the pockets. More particularly, the pockets can be voids extending proximally from the distal face 323, and thus, provide openings in the distal face 323. The pockets can be sized such that the distal section 314 containing the pockets is flexible.

Figure 8B:
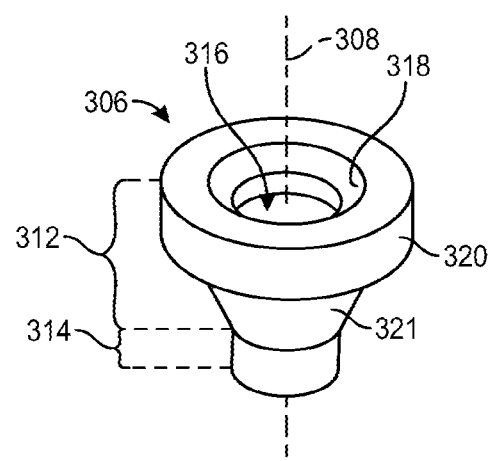
Figure 9A:
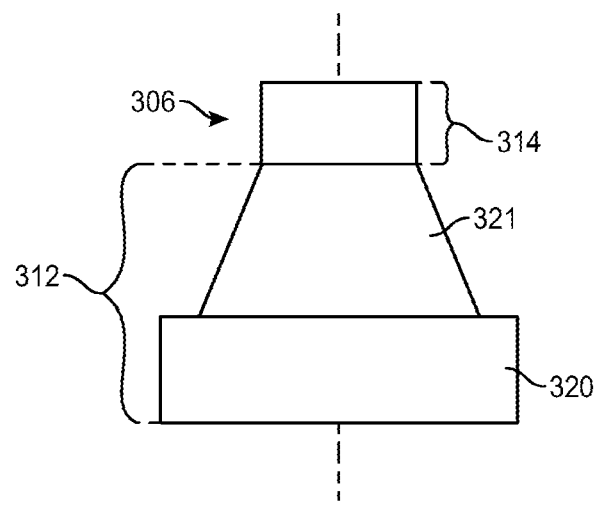
FIGS. 9A and 9B are a longitudinal side elevation view and a longitudinal cross-sectional side view, respectively, of a seal in accordance with the present disclosure.
Figure 9B:
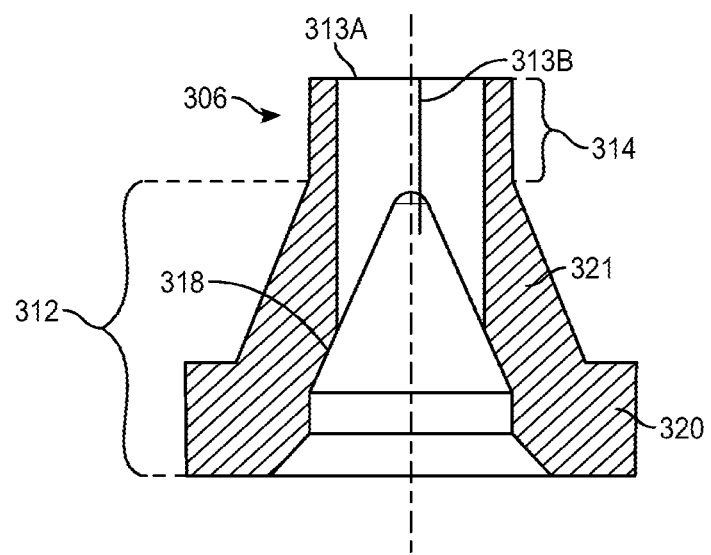

Referring to FIG. 8B, and FIG. 9A-9B, the seal 306 may include a proximal opening 316 and a tapered inner surface 318 extending distally from the proximal opening 316. The opening 316 can taper toward the longitudinal axis 308. The tapered inner surface 318 generally distributes force incurred by advancing larger objects through the seal 306, and directs such forces in a radial direction. In certain implementations, a portion of the tapered inner surface 318 may extend through the proximal section 312. Slits 313A, 313B can extend through a portion of the tapered inner surface 318. In general, the tapered inner surface 318 helps to center objects during insertion through the seal 306, thereby reducing a likelihood of premature damage to the seal 306, while also reducing a likelihood of fluid leakage from the seal 306 during insertion and removal of objects through the seal 306.

In certain implementations, the seal 306 is made of a silicone rubber having a durometer from and including 10 Shore OO to and including 20 Shore A. In some embodiments, different areas of the seal 306 may be formed from different materials, each having a different hardness. For example, in one implementation, the proximal section 312, including the tapered body 321, may be formed from a material having a durometer of 20 Shore A while the distal section 314 may be formed of a material having a durometer of 30 Shore OO. In such implementations, the hard durometer of the proximal section 312 prevents excessive elongation during advancement, while the soft durometer of the distal section 314 allows it to fill gaps and easily stretch in order to maintain a seal against an object inserted through the seal 306.

Figure 10:
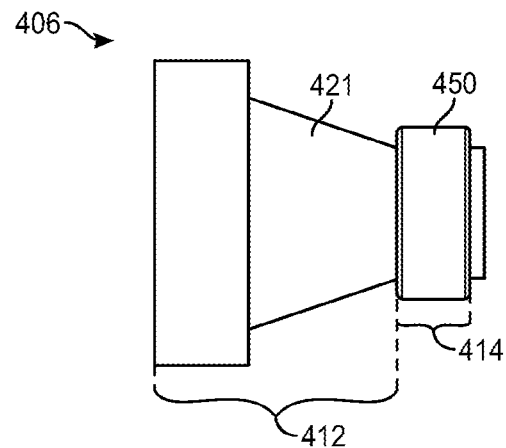
FIG. 10 is a longitudinal side elevation view of a seal in accordance with the present disclosure.

Referring to FIG. 10, a longitudinal side elevation view of a seal is shown in accordance with the present disclosure. A seal 406 can be used in place of the seals described above (206, 306) within the introducer hub assemblies described above (200, 300). For the avoidance of doubt, any of the seals described herein may be used in any of the introducer hub assemblies and/or leadless pacemaker systems described herein. To improve sealing against objects inserted through them, seals in accordance with the present disclosure may include a biasing element adapted to maintain pressure and bias the distal section of the seals inward. More particularly, the biasing element can bias the slits of the seal 406 into a closed state. The biasing element can be a band, a ring, a coil, or another component that exerts a compressive force on a distal section 414, as described below. The seal 406 includes a proximal section 412 having a tapered body 421 and the distal section 414 through which slits (not shown) extend. The seal 406 can include a biasing element 450 having an elastomeric band or an elastic ring disposed about the distal section 414. The biasing element 450 can bias segments of the distal section 414 together. For example, the biasing element can be an annulus having an inner diameter in a relaxed state that is less than an outer diameter of the distal section 414 in a relaxed state. Thus, a press fit is formed between the annulus and the distal section, and the annulus presses radially inward on an outer surface of the distal section. During experimental testing, it was found that minimal leaking about a wire having 0.035 inches diameter was achieved through such an arrangement when a fluid stopped by the seal 406 had a pressure range of 0 pounds per square inch to 30 pounds per square inch. The tapered section 421 can be made from a material having a durometer of 20 Shore A, and the distal section 414 can be made from a material having a durometer of 30 Shore OO. The elastomeric band 450 can be formed from a material having a durometer of 20 Shore A.

Figure 11:
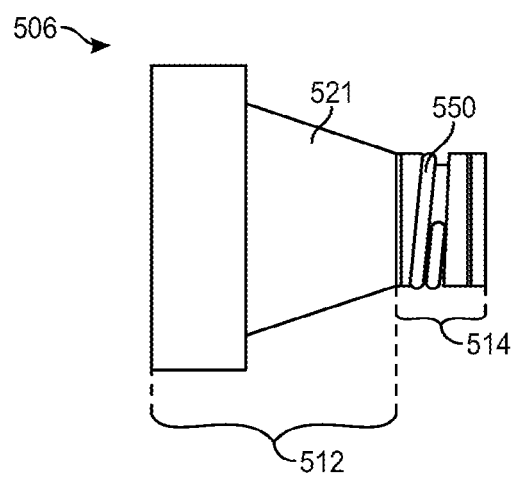
FIG. 11 is a longitudinal side elevation view of a seal in accordance with the present disclosure.

Referring to FIG. 11, a longitudinal side elevation view of a seal is shown in accordance with the present disclosure. A seal 506 can be used in place of the seals described above (206, 306, 406) within the introducer hub assemblies described above (200, 300). The seal 506 can include a proximal section 512 having a tapered body 521 and a distal section 514 through which slits (not shown) extend. The seal 506 further includes a biasing element 550, e.g., a spring element, disposed about the distal section 514 to bias segments of the distal section 514 together. Spring element 550 can be a spring coil over the cylindrical segment. The spring coil can extend over distal section 514 to the tapered body 521. Accordingly, the spring coil can extend around the slit seal. Like the annular biasing element 450 described above, the coil 550 can wrap around the outer surface of the distal section 450 and press radially inward to close the slits of the seal.

Figure 12A:
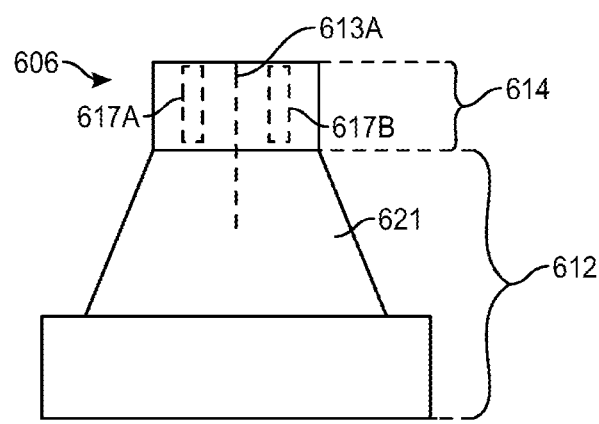
FIGS. 12A and 12B are a longitudinal side elevation view and a distal plan view, respectively, of a seal in accordance with the present disclosure.

Referring to FIG. 12A, a longitudinal side elevation view of a seal is shown in accordance with the present disclosure. A seal 606 can be used in place of the seals described above (206, 306, 406, 506) within the introducer hub assemblies described above (200, 300). The seal 606 includes a proximal section 612 having a tapered body 621 and a distal section 614 through which slits 613A, 613B extend. In an embodiment, the seal 606 further includes magnets disposed within the distal section 614. For example, in the side view, magnets 617A and 617B (indicated by hidden lines) are arranged such that the magnet axes extend parallel to longitudinal axis 308 on opposite sides of a plane containing slit 613A. The magnets are separated in the transverse direction, however, may be located close enough to each other to attract each other in the transverse direction. The attracted magnets can apply a load against the distal section 614 that the magnets are disposed within, and thus, can bias segments of the distal section 614 together.

Figure 12B:
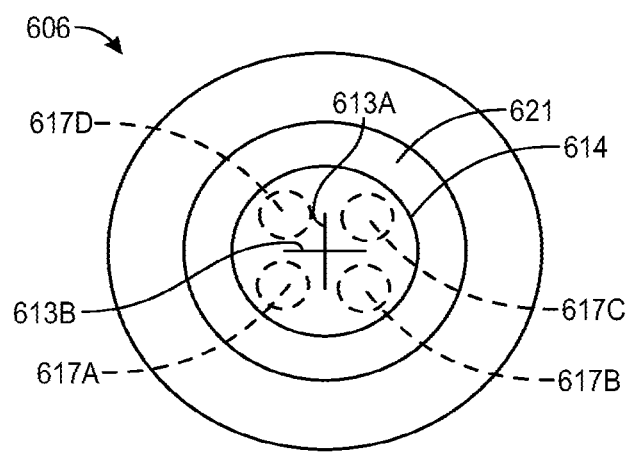

Referring to FIG. 12B, a distal plan view of a seal is shown in accordance with the present disclosure. Two or more magnets can be arranged about the longitudinal axis 308. For example, four magnets may be embedded or disposed within the distal section 614 in respective quadrants. The quadrants can be defined by the cross slits 613A, 613B that intersect along the longitudinal axis 308. The magnets may be equally spaced, e.g., each magnet may be placed at a corner of a square reference geometry, and thus, the magnets may attract each other with approximately equal forces. The magnets can exert an overall inward force on the distal section 614 to bias the seal slits toward a closed state. In implementations of seals including magnets, the biasing force of the magnets may be varied by changing, among other things: one or more of the durometers of the material of distal section 614; the number; the size; the shape, and/or the spacing of the magnets. Although illustrated in FIGS. 12A-12B as being cylindrical, spherical, cylindrical, rectangular, or any other suitable shape of magnet may be used. In certain implementations, the magnets may be molded into the seal. In other implementations, the magnets may be inserted after molding of the seal or otherwise coupled to the seal.

Figure 13A:
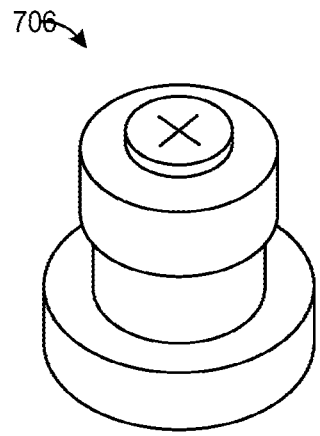
FIG. 13A is a photograph of a seal in accordance with the present disclosure.

Referring to FIG. 13A, a photograph of a seal is shown in accordance with the present disclosure. A seal 706 can be used in place of the seals described above (206, 306, 406, 506, 606) within the introducer hub assemblies described above (200, 300). The photograph of the seal 706 is in an unused state. In the unused state, the cross-slits of the seal 706 can be in the closed state. More particularly, the distal section and/or the proximal section of the seal may be closed to the ingress of fluids from an external environment. As described above, a biasing element can exert a radially inward force on one or more of the seal sections to bias the slits toward the closed state in order to resist hemostatic pressure of the external environment. For example, the biasing element can apply an inward force to the distal section of the seal 706.

Figure 13B:
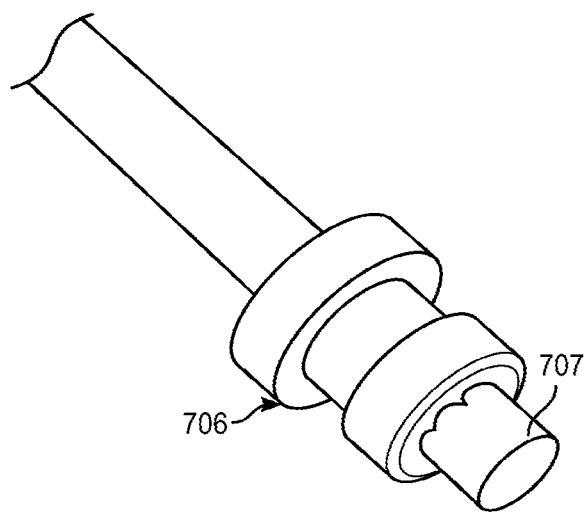
FIG. 13B is a photograph of the seal of FIG. 13A with a secondary introducer extending therethrough in accordance with the present disclosure.

Referring to FIG. 13B, a photograph of the seal of FIG. 13A with a secondary introducer extending therethrough is shown in accordance with the present disclosure. The photograph is of the seal 706 with a 0.300" secondary introducer device 707 inserted through the seal 706. When the secondary introducer device 707 is inserted into the seal 706, the slits expand into an open state. In the open state, the introducer device 707 can pass from a proximal end of the introducer hub assembly containing the seal 706 to the distal end of the introducer hub assembly. The expanded seal, however, can press inward against an outer surface of the introducer device 707. The inward pressure can form a seal between the slits and the outer surfaces. The seal resists leakage of fluids, e.g., blood, through the surface interface.

Figure 14A:
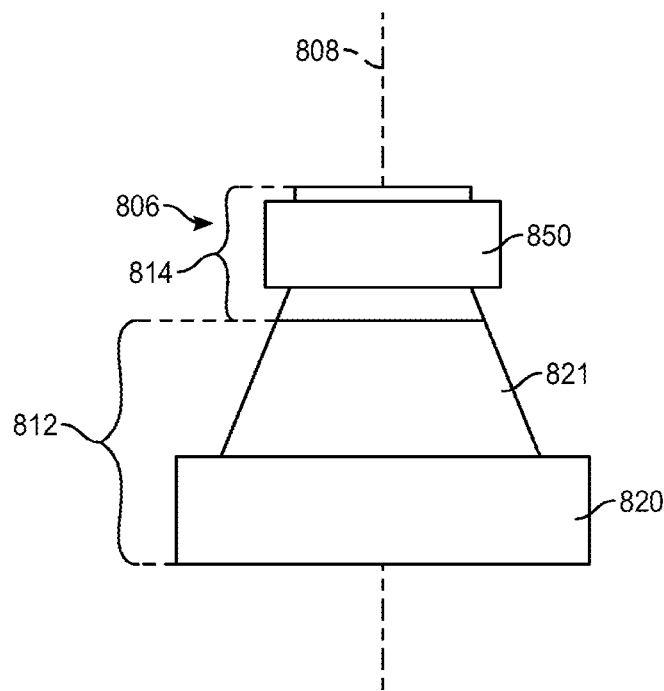
FIGS. 14A and 14B are a side elevation view and a cross-sectional side view, respectively, of a seal in accordance with the present disclosure.

Referring to FIG. 14A, a side elevation view of a seal is shown in accordance with the present disclosure. A seal 806 can be used in place of the seals described above (206, 306, 406, 506, 606, 706) within the introducer hub assemblies described above (200, 300). The seal 806 generally includes a first, proximal section 812 and a second, distal section 814 adjacent to the proximal section 812. In certain implementations, the proximal section 812 further includes a proximal flange 820 and a tapered body 821 and the distal section 814 is a substantially cylindrical body adjacent to the tapered body 821.

Figure 14B:
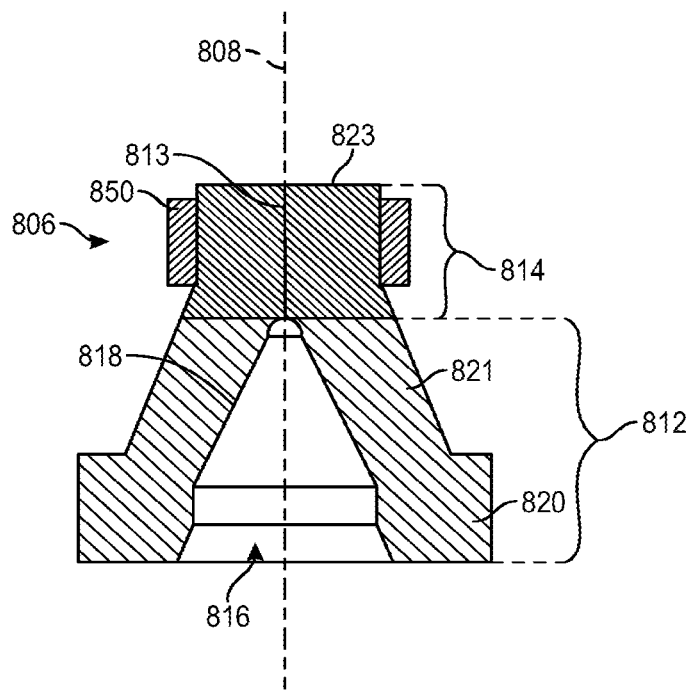

Referring to FIG. 14B, a cross-sectional side view of a seal is shown in accordance with the present disclosure. The seal 806 may include a proximal opening 816 and a tapered inner surface 818 extending distally from the proximal opening 816 and tapering toward a longitudinal axis 808. The tapered inner surface 818 generally distributes force incurred by advancing larger objects through the seal 806, and directs such forces in a radial direction. In contrast to the slits of the previously discussed implementations, the seal 806 includes a bore 813 extending from a distal end of the tapered inner surface 818 and through the distal section 814 to a distal face 823 of the distal section 814. The seal 806 further includes an elastomeric ring 850 disposed about the distal section 814 to impart an inward force on distal section 814 and the bore 813. The force can bias the seal 806 into a closed state.

The distal section 814 and the proximal section 812 are composed of two different materials and, in particular, materials having different durometers. In general, the distal section 814 may be formed from a softer and/or more compliant material than the proximal section 812. The increased compliance of the distal section 814 relative to the proximal section 812 can improve sealing of the distal section 814 about an object inserted through the bore 813. Conversely, the proximal section 812 of the seal 806 may be formed of a harder material in order to impart additional resiliency and durability to withstand the initial insertion of such objects. For example, in certain implementations, the distal section 814 may be formed of a first silicone material having a durometer of 30 Shore A while the proximal section 812 may be formed from a second silicone material having a durometer greater than 30 Shore A, e.g., 40 Shore A or above. As in the previously discussed implementations, the materials of the seal 806 may also be selected to be at least one of self-healing and self-lubricating.

The bore 813 may generally be formed during manufacturing by first molding the distal section 814 as a solid piece and then puncturing the molded distal section 814. In certain implementations, puncturing the distal section 814 may be performed by inserting a series of puncturing tools through the distal section 814. In general, such tools are inserted in order of increasing diameter or width until a predetermined maximum diameter is reached. The predetermined diameter may, in certain implementations, correspond to a diameter of an object to be inserted through the seal. In certain implementations, the predetermined maximum diameter may be less than the maximum diameter of the object to improve the seal of the distal section 812 against the object when it is inserted.

Figure 15:
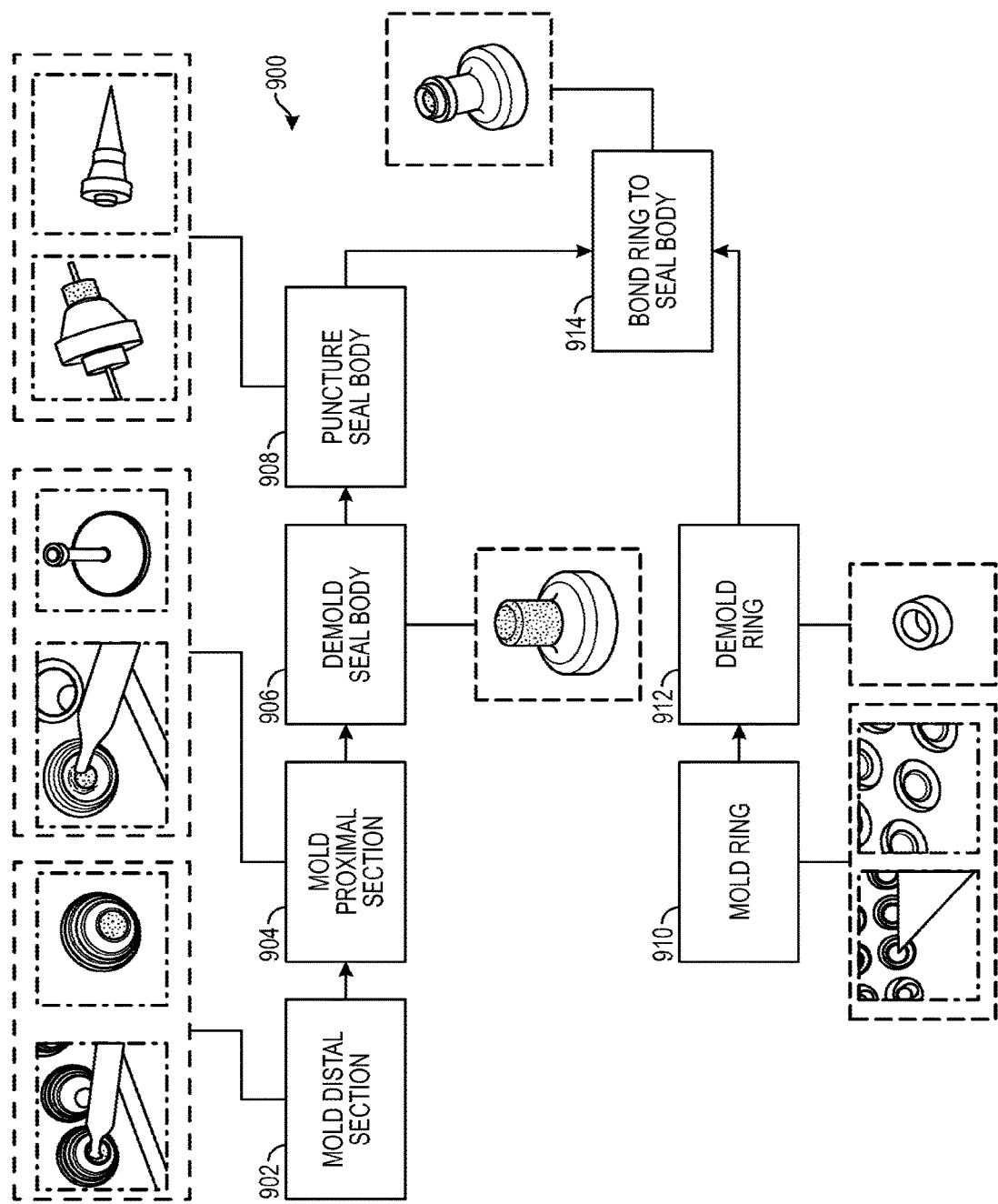
FIG. 15 is a flow chart illustrating a method of manufacturing a seal in accordance with the present disclosure.

Referring to FIG. 15, a flow chart illustrating a method of manufacturing a seal is shown in accordance with the present disclosure. A flow chart 900 illustrates a manufacturing process that may be used to produce a seal, such as the seal 806 of FIGS. 14A-14B. In general, the process includes molding the proximal and distal sections of the seal 812, 814 to form a seal body that is then punctured. The ring 850 may be separately molded and then bonded to the seal body, thereby forming the completed seal 806.

At operation 902, the distal section 814 of the seal 800 is molded. For example, in certain implementations, a first material may be poured into a mold, partially filling the mold to a level corresponding to the length of the distal section. The first material may then be allowed to cure within the mold, forming the distal section 814. Although various materials may be used, in certain implementations, the first material may be a two-part liquid silicone rubber having a durometer of 30 Shore 00.

At operation 904, the proximal section 812 of the seal 800 is molded. For example, in certain implementations, a second material may be poured into the mold on top of the molded distal section 814. A cap or mold half may then be coupled to the mold in order to form the proximal face of the proximal section 812. The cap or mold half may include a conical or similar shape in order to form the tapered inner surface 818 of the proximal section 812. The proximal section 812 may then be left to cure as required. Accordingly, the proximal section 812 can be molded onto the distal section 814. Again, while other materials may be used, the second material may, in certain implementations, be a two-part liquid silicone rubber having a durometer of 30 Shore A.

At operation 906, the completed seal body is demolded. As illustrated in the photograph accompanying operation 906, the seal body is generally a unitary or monolithic part with the proximal section 812 integrally formed with the distal section 814.

At operation 908, the seal body is punctured to form the bore 813 of the seal 806. As previously noted, the process of puncturing the seal body may include the use of multiple puncturing tools. For example, as illustrated in the photographs accompanying operation 908, the seal body may first be punctured with a first puncturing tool, e.g., a sharp needle or a rod, then subsequently punctured using a second puncturing tool, e.g., a blunt conical tool. In other implementations, needles, or rods having progressively larger diameters or widths may be used to puncture the seal body until the required bore size is achieved. For example, the first puncturing tool having a first diameter can be used to puncture the distal section of the seal, and then a second puncturing tool having a second diameter greater than the first diameter can be used to puncture the distal section.

It will be appreciated that in certain embodiments, the operations may be modified. For example, to form the seal 206 having cross-slits, a razor blade may be used. The razor blade can form two or more slits in a cross pattern, e.g., perpendicular to one another, to create the slit seal section (s).

In a separate process, the ring 850 may be molded. At operation 910, for example, a ring material may be injected into a mold, cured, and subsequently demolded at operation 912. In certain implementations, the ring material may be a two-part silicone rubber having a durometer of 20 Shore A. Following demolding, the ring 850 may be attached to the seal body at operation 914. In certain implementations, the ring 850 may be bonded to the seal body using an adhesive suitable for the particular materials used to form the ring 850 and the distal section 814. For example, silicone rubber based materials may be bonded using a silicone adhesive, such as Sil-Poxy®. Bonding of the ring 850 to the distal section 814 may further include a curing period to allow the adhesive to cure.

Any of the molding operations 902, 904, 910 may include a degassing operation in which the liquid material is placed in a vacuum or low pressure environment prior to or during curing. By doing so, air or similar gases may be removed from the molded parts, reducing variation and improving consistency of the final seal 806. Also, any of the curing operations discussed above may include, among other things, placement of the part being cured into an oven or similar heated environment to speed up the curing process.

As for additional details pertinent to the present disclosure, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A hemostatic seal, comprising:
   a seal body including a proximal section having a conical body and a distal section having a cylindrical body, a tapered bore extending longitudinally through the conical body, and a slit extending longitudinally through the cylindrical body from the tapered bore; and
   an elastomeric ring disposed about the cylindrical body radially around the slit to exert a radially compressive force uniformly distributed about the distal section to bias the distal section inward, wherein the conical body and the elastomeric ring are harder than the cylindrical body.

2. The hemostatic seal of claim 1, wherein the elastomeric ring includes a circular ring.

3. The hemostatic seal of claim 2, wherein the circular ring is bonded to the distal section.

4. The hemostatic seal of claim 1, wherein the tapered bore narrows in a distal direction.

5. The hemostatic seal of claim 1, wherein the conical body and the elastomeric ring are formed from a first material, and wherein the cylindrical body is formed from a second material different than the first material.

6. The hemostatic seal of claim 5, wherein the first material has a higher durometer than the second material.

7. The hemostatic seal of claim 1, wherein a second slit extends through the cylindrical body, and wherein the second slit crosses the slit.

8. An introducer hub assembly, comprising:
   an introducer hub having a longitudinal axis;
   a hub cap coupled to a proximal end of the introducer hub; and
   a hemostatic seal between the hub cap and the introducer hub, wherein the hemostatic seal includes
   a seal body including a proximal section having a conical body and a distal section having a cylindrical body, a tapered bore extending longitudinally through the conical body, and a slit extending longitudinally through the cylindrical body from the tapered bore, and
   an elastomeric ring disposed about the cylindrical body radially around the slit to exert a radially compressive force uniformly distributed about the distal section to bias the distal section inward, wherein the conical body and the elastomeric ring are harder than the cylindrical body.

9. The introducer hub assembly of claim 8, wherein the elastomeric ring includes a circular ring.

10. The introducer hub assembly of claim 9, wherein the circular ring is bonded to the distal section.

11. The introducer hub assembly of claim 8, wherein the tapered bore narrows in a distal direction.

12. The introducer hub assembly of claim 8, wherein the conical body and the elastomeric ring are formed from a first material, and wherein the cylindrical body is formed from a second material different than the first material.

13. A leadless pacemaker system, comprising:
- a deflectable catheter;
- a guide catheter mounted on the deflectable catheter; and
- an introducer hub assembly mounted on the guide catheter, wherein the introducer hub assembly includes a hemostatic seal including
  - a seal body including a proximal section having a conical body and a distal section having a cylindrical body, a tapered bore extending longitudinally through the conical body, and a slit extending longitudinally through the cylindrical body from the tapered bore, and
  - an elastomeric ring disposed about the cylindrical body radially around the slit to exert a radially compressive force uniformly distributed about the distal section to bias the distal section inward, wherein the conical body and the elastomeric ring are harder than the cylindrical body.

14. The leadless pacemaker system of claim 13, wherein the elastomeric ring includes a circular ring.

15. The leadless pacemaker system of claim 14, wherein the circular ring is bonded to the distal section.

16. The leadless pacemaker system of claim 13, wherein the conical body includes a tapered inner surface around the tapered bore, and wherein the tapered bore narrows in a distal direction.

17. The leadless pacemaker system of claim 13, wherein the conical body and the elastomeric ring are formed from a first material, and wherein the cylindrical body is formed from a second material different than the first material.

* * * * *